United States Patent
Woelfle et al.

(10) Patent No.: US 9,309,218 B2
(45) Date of Patent: Apr. 12, 2016

(54) 2-OXO-1,3-DIOXOLANE-4-CARBOXAMIDES, THEIR PREPARATION AND USE

(71) Applicant: Construction Research & Technology GmbH, Trostberg (DE)

(72) Inventors: Heimo Woelfle, Traunstein (DE); Burkhard Walther, Garching (DE); Maximilian Köhler, Trostberg (DE); Sophie Putzien, Ampfing (DE)

(73) Assignee: Construction Research & Technology GmbH, Trostberg (DE)

( * ) Notice: Subject to any disclaimer, the term of this patent is extended or adjusted under 35 U.S.C. 154(b) by 0 days.

(21) Appl. No.: 14/364,413

(22) PCT Filed: Nov. 14, 2012

(86) PCT No.: PCT/EP2012/072589
§ 371 (c)(1),
(2) Date: Jun. 11, 2014

(87) PCT Pub. No.: WO2013/092011
PCT Pub. Date: Jun. 27, 2013

(65) Prior Publication Data
US 2015/0051365 A1    Feb. 19, 2015

(30) Foreign Application Priority Data
Dec. 22, 2011 (EP) .................................. 11195272

(51) Int. Cl.
*C08G 18/81* (2006.01)
*C07D 317/08* (2006.01)
(Continued)

(52) U.S. Cl.
CPC ............ *C07D 317/34* (2013.01); *C07C 231/12* (2013.01); *C07C 269/04* (2013.01);
(Continued)

(58) Field of Classification Search
CPC .. C07C 231/01; C07C 269/04; C07C 329/04; C07D 317/34; C07D 317/382; C08G 18/8061; C08G 18/71; C08G 18/73; C08G 18/792; C08G 18/281; C08G 64/0241; C08G 64/38
USPC ................... 528/45; 549/229; 558/248, 276; 560/165
See application file for complete search history.

(56) References Cited

U.S. PATENT DOCUMENTS
7,968,572 B2    6/2011    Nakai et al.
8,044,194 B2    10/2011   Dubois et al.
(Continued)

FOREIGN PATENT DOCUMENTS
EP    0 001 088 A1    3/1979
EP    1 941 946 A1    7/2008
(Continued)

OTHER PUBLICATIONS

PCT/EP2012/072589—International Search Report, mailed on Jan. 4, 2013.
(Continued)

*Primary Examiner* — T. Victor Oh
(74) *Attorney, Agent, or Firm* — Curatolo Sidoti Co., LPA; Joseph G. Curatolo; Salvatore A. Sidoti

(57) ABSTRACT

The present invention suggests 2-oxo-1,3-dioxolane-4-carboxamides of formula (I),

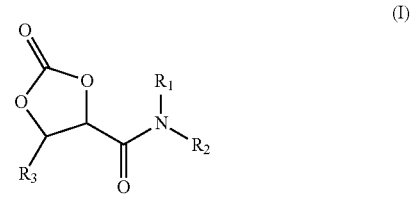

in which $R_2$ can be, inter alia, an n-valent radical (n>1) which is substituted with n−1 further 2-oxo-1,3-dioxolane-4-carboxamide groups of general formula (II),

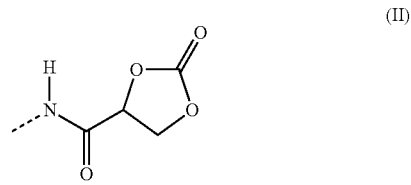

to processes for the preparation of these 2-oxo-1,3-dioxolane-4-carboxamides, to processes for the preparation of the 2-oxo-1,3-dioxolane-4-carboxylic acids of formula (III),

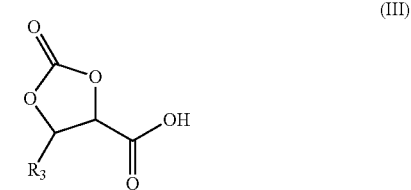

which are suitable starting materials for the above processes, and to the use of said 2-oxo-1,3-dioxolane-4-carboxamides for the preparation of (poly)hydroxyurethanes, -hydroxycarbonates and -hydroxysulfanylformates, and also as end groups for the blocking of amines.

18 Claims, No Drawings

(51) Int. Cl.

| | |
|---|---|
| *C07C 329/00* | (2006.01) |
| *C07C 69/96* | (2006.01) |
| *C07C 261/00* | (2006.01) |
| *C07D 317/34* | (2006.01) |
| *C07D 317/38* | (2006.01) |
| *C08G 18/71* | (2006.01) |
| *C08G 18/73* | (2006.01) |
| *C08G 18/79* | (2006.01) |
| *C08G 18/28* | (2006.01) |
| *C08G 64/02* | (2006.01) |
| *C08G 64/38* | (2006.01) |
| *C07C 231/12* | (2006.01) |
| *C07C 269/04* | (2006.01) |
| *C07C 329/04* | (2006.01) |
| *C08G 18/80* | (2006.01) |

(52) U.S. Cl.
CPC .......... *C07C329/04* (2013.01); *C07D 317/38* (2013.01); *C08G 18/281* (2013.01); *C08G 18/71* (2013.01); *C08G 18/73* (2013.01); *C08G 18/792* (2013.01); *C08G 18/8061* (2013.01); *C08G 64/0241* (2013.01); *C08G 64/38* (2013.01)

(56) References Cited

U.S. PATENT DOCUMENTS

| | | |
|---|---|---|
| 2010/0317838 A1 | 12/2010 | Dubois et al. |
| 2011/0313177 A1 | 12/2011 | Mecfel-Marczewski et al. |
| 2014/0228583 A1 | 8/2014 | Mecfel-Marczewski et al. |

FOREIGN PATENT DOCUMENTS

| | | |
|---|---|---|
| EP | 2 397 474 A1 | 12/2011 |
| JP | 7-285960 A | 10/1995 |
| JP | 2006003433 A | 1/2006 |
| WO | WO 2004/003001 A1 | 1/2004 |
| WO | WO 2007/040208 A1 | 4/2007 |
| WO | WO 2011/157551 A1 | 12/2011 |

OTHER PUBLICATIONS

PCT/EP2012/072589—International Written Opinion, mailed on Jan. 4, 2013.
PCT/EP2012/072589—International Preliminary Report on Patentability, mailed on Jun. 24, 2014.
Tomita, et al., "Model Reaction for the Synthesis of Polyhydroxyurethanes from Cyclic Carbonates with Amines: Substituent Effect on the Reactivity and Selectivity of Ring-Opening Direction in the Reaction of Five-Membered Cyclic Carbonates with Amine", Journal of Polymer Science, 2001, vol. 39, pp. 3678-3685, John Wiley & Sons Inc.
Lewis, et al., "Synthesis of L-660,631 Methyl Ester and Related Compounds", Tetrahedron Letters, Jan. 1, 1988, vol. 29, No. 19, pp. 2279-2282, Pergamon Press PLC, Great Britain.
Diakoumakos, Constantino, et al., "Non-Isocyanate-Based Polyurethanes Derived upon the Reaction of Amines with Cyclocarbonate Resins", Macromol. Symp., 2004, vol. 216, pp. 37-46.
Petit, Y., et al., "Ethyl Glycidate From (S)-Serine: Ethyl (R)-(+)-2,3-Epoxypropanoate", Organic Synthesis Collection, 2004, vol. 10, p. 401; Organic Syntheses, 1998, vol. 75, p. 37.
Stevenson, Christian P., et al., "Preparation of (S)-Methyl Glycidate VIA Hydrolytic Kinetic Resolution", Organic Syntheses, 2006, vol. 83, pp. 162-169; Organic Syntheses Collection, 2009, vol. 11, pp. 157-163.

2-OXO-1,3-DIOXOLANE-4-CARBOXAMIDES, THEIR PREPARATION AND USE

CROSS REFERENCE TO RELATED APPLICATIONS

This application is a national stage application of International Application No. PCT/EP2012/072589, filed 14 Nov. 2012, which claims priority from European Patent Application No. 11195272.7, filed 22 Dec. 2011, from which applications priority is claimed, and which are incorporated herein by reference.

The present invention relates to 2-oxo-1,3-dioxolane-4-carboxamides of formula (I),

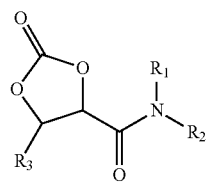
(I)

in which $R_2$ can be, inter alia, an n-valent radical (n>1), which is substituted with n−1 further 2-oxo-1,3-dioxolane-4-carboxamide groups of general formula (II),

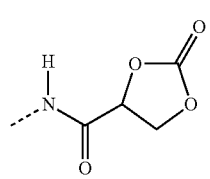
(II)

to processes or the preparation of these 2-oxo-1,3-dioxolane-4-carboxamides, to processes for the preparation of the 2-oxo-1,3-dioxolane-4-carboxylic acids of formula (III),

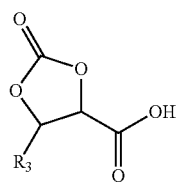
(III)

which are suitable starting materials for the above processes, and to the use of said 2-oxo-1,3-dioxolane-4-carboxamides for the preparation of (poly)hydroxyurethanes, -hydroxycarbonates and -hydroxysulfanylformates, and also as end groups for the blocking of amines.

Structurally similar compounds are already known in the prior art. For example, WO 2004003001 A1 describes compounds of the general formula (VI)

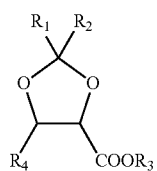
(VI)

where $R_1$ and $R_2$ may be radicals independent of one another, $R_1+R_2=O$ or $CR_1+R_2$ may be a 3-6-membered cycloalkyl group. $R_4$ may be hydrogen, straight-chain or branched $C_{1-8}$-alkyl, $C_{5-12}$-cycloalkyl or $C_{6-15}$-aryl. $R_3$ may be straight-chain or branched $C_{1-8}$-alkyl or $C_{6-15}$-aryl. In general, WO 2004/003001 A1 describes the enzymatic race-mate separation of the enantiomers of type (VI) but without indicating a synthesis for these compounds.

EP 1941946 A1 describes the use of a carbonitride catalyst inter alia for the preparation of certain disubstituted organic carbonates. These may also be compounds of the general formula (VII),

(VII)

where $R^{10}$ and $R^{11}$, independently of one another, are selected optional substituents. Possible meanings of the substituents are alkyl, aryl, herteroaryl and ester groups $CO_2A$, where A may in turn be alkyl or aryl, e.g. straight-chain or branched $C_{1-6}$-alkyl, preferably $C_{1-3}$-alkyl and particularly preferably methyl or ethyl. However, no syntheses for 2-oxo-1,3-dioxolane systems are stated.

JP 2006-003433 A discloses a sealing composition for liquid crystal display elements which comprises a compound of the general formula (VIII),

(VIII)

where R is H, a hydroxyl group, a cyano group, a carboxylic acid group, an optionally substituted aromatic ring, a straight-chain, branched or cyclic alkyl group, an acyl group or an ester group. The 2-oxo-1,3-dioxolane-4-carboxylic acid (R=COOH) is also mentioned.

EP 0001088 A1 describes inter alia 2-oxo-1,3-dioxolanes of the general formula (IX), where R can be H or $CH_3$,

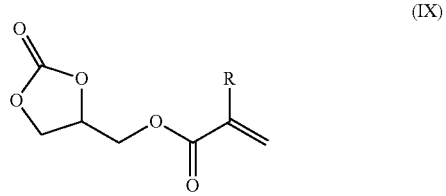
(IX)

EP 2397474 A1 describes 2-oxo-1,3-dioxolane-4-carboxylic acid esters of formula (X)

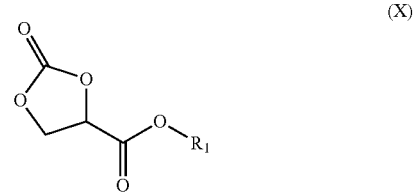
(X)

in which $R_1$ may preferably be Me or Et or an n-valent radical when may be substituted with a maximum of n−1 further 2-oxo-1,3-dioxolane-4-carboxyl groups, a process for their preparation by means of carboxylation of the corresponding epoxides, a process for their transesterification, and also their use for the preparation of hydroxyurethanes and as end groups for the blocking of amines.

US 20100317838 A1 describes compounds of formula (XI)

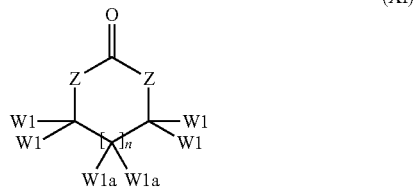

in which Z=O and n=0, at least one of the radicals W1 or W1a comprises a protected glycoside, and each of the radicals W1 and W1a, independently of one another, may inter alia also be an amide group. The difference with respect to the present invention is that, in accordance with the invention no protected glycoside groups are provided.

Polyurethanes based on polyisocyanates belong to the prior art. These are used for example as adhesives, sealants, casting compositions, as corrosion protection and for coatings. The high resistance to acids, alkalis and chemicals of the cured compositions obtained in this way are advantageous. However, monomeric low molecular weight (poly)isocyanate compounds are toxicologically unacceptable, especially if they are readily volatile or migrate.

Polyurethane systems can also be obtained starting from cyclic carbonate compounds, which are toxicologically acceptable. Thus, for instance, glycerol carbonate (4-(hydroxymethyl)-2-oxo-1,3-dioxolane) is regularly used in cosmetics.

Cyclic carbonate compounds react with amines with ring opening inter alia to give hydroxyurethanes (cf. formula scheme below):

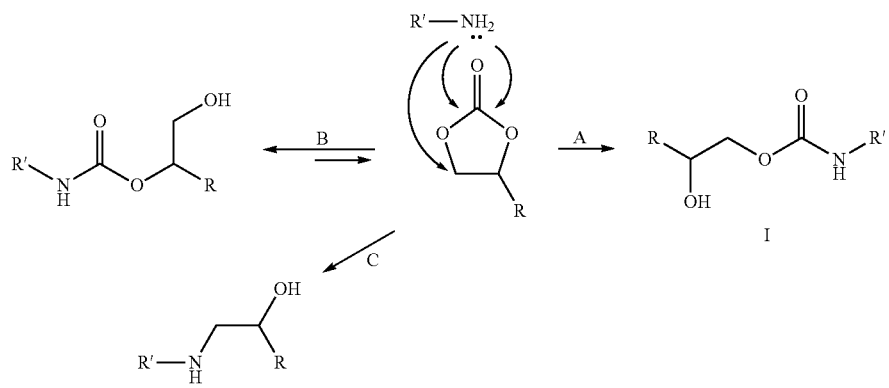

Disadvantages of the systems based on glycerol carbonate are the low regioselectivity, which leads to reaction pathways A, B and C, the comparatively low reactivity of the systems at room temperature, and the fact that catalysts which increase the rate of the ring opening obviously also promote the back-reaction, which can lead to a partial decomposition of the products already formed.

In the aforementioned EP 2397474 A1, these problems have been partially solved by using an ester group instead of an ether group in R. This electron-withdrawing group led to a considerable increase in the rate of the reaction and to a preference for reaction pathway A. In the case of the secondary hydroxyurethanes [I] formed, no back-reaction was observed. However, the production of binders which comprise two or more 2-oxo-1,3-dioxolane-4-carboxyl groups in the molecule is difficult since this takes place via a transesterification, during which the cyclocarbonate ring can also be attacked.

The aforementioned US 20100317838 A1 gives the impression that this ring opening reaction is independent of the nature of R (cf. claim 17 of US 2010/0317838 A1 which is directed to the ring opening of compounds of claim 1 which may contain ester groups or amide groups alike). However, this impression is quite misleading.

Firstly, studies have been carried out (cf. H. Tomita, F. Sanda, T. Endo. Journal of Polymer Science: Part A: Polymer Chemistry, Vol. 39, 3678-3685 (2001)) according to which the reactivity of the 2-oxo-1,3-dioxolanes, which are substituted in 4-position with the group R, with amines increases in the order: R=Me<R=H<R=Ph<R=CH$_2$OPh<<R=CF$_3$.

Secondly, in the case of the products of the aforementioned EP 2397474 A1 where the polymeric main chain is attached through ester bonds, i.e. R in the formula scheme below means the polymeric main chain, the ring opening (hardening) reaction is accompanied by a certain amount of aminolysis of the ester bond leading to the detachment of the main chain in the form of an unreactive alcohol.

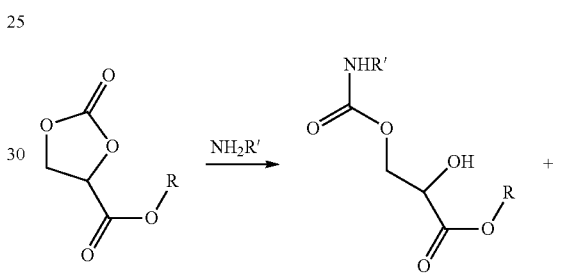

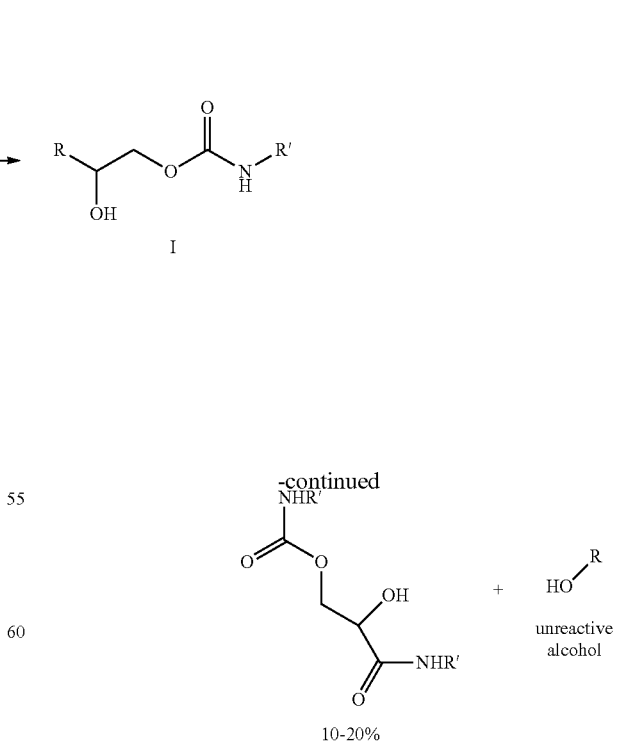

It was the object of the present invention to essentially avoid at least some of the disadvantages of the prior art described above. In general terms, the aim was to provide an alternative 2-oxo-1,3-dioxolane system with an electron-withdrawing group. In particular, the aim was to provide a 2-oxo-1,3-dioxolane system which is toxicologically acceptable, readily accessible and highly reactive with amine hardeners and is moreover suitable as a crosslinkable binder (with a bonding to the polymer chain which is less prone to attack by amines).

This object has been achieved with the features of the independent claims. The de-pendent claims relate to preferred embodiments.

In the case of the amides of the present invention aminolysis is per se not possible. If any transamination occurred, the formed amine would be capable of acting as a reactive hardener to attack further cyclic carbonate groups. Crosslinking and hardening of the products are thus much higher. This follows from the formula scheme below and will be demonstrated in the experimental section hereinbelow.

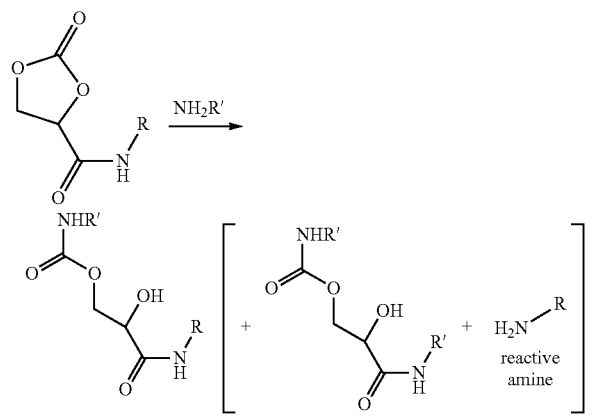

The present invention provides a 2-oxo-1,3-dioxolane-4-carboxamide of formula (I),

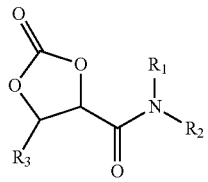

which is characterized in that $R_1$ and $R_2$, in each case independently of one another, are selected from H, straight-chain, branched or cyclic $C_{1-12}$-alkyl groups, $C_{6-10}$-aryl groups, $C_{6-12}$-aralkyl groups and $C_{6-12}$-alkaryl groups or, together with the N atom to which they are bonded, form a 5- to 8-membered ring, and $R_3$ is selected from H and straight-chain, branched or cyclic $C_{1-12}$-alkyl groups, or $R_1$ and $R_3$ are each H, and $R_2$ is an n-valent radical, wherein n is an integer greater than 1, which is substituted with n–1 further 2-oxo-1,3-dioxolane-4-carboxamide groups of general formula (II)

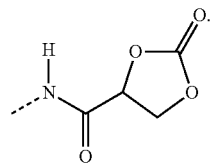

The carbon atom to which $R_3$ is bonded can additionally also carry a further $C_{1-12}$-alkyl group. The carbon atom in the 4 position can also additionally carry a $C_{1-12}$-alkyl group. Both may be the case at the same time.

In the 2-oxo-1,3-dioxolane-4-carboxamide of the invention the groups $R_1$ and $R_3$ are preferably each H, and $R_2$ is selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, phenyl and benzyl.

The 2-oxo-1,3-dioxolane-4-carboxamides of the invention can be used as curable binders. In this case, a functionality with regard to the 2-oxo-1,3-dioxolane group of greater than 1 is required (as defined hereinabove). Preferably, n can be 2 to 5, in particular 2 to 3.

In this case $R_2$ is the polymeric backbone of the curable binder and is selected from straight-chain or branched $C_{2-22}$-alkylene groups, polyether groups of the general formula $-(A_1O)_m-$, wherein $A_1$ is $C_{2-5}$-alkylene and m is 1-100, polycarbonate groups, polyester groups, poly(meth)acrylate groups, and combinations thereof.

Key intermediates in the preparation of the 2-oxo-1,3-dioxolane-4-carboxamides (I) according to the invention are 2-oxo-1,3-dioxolane-4-carboxylic acids of formula (III).

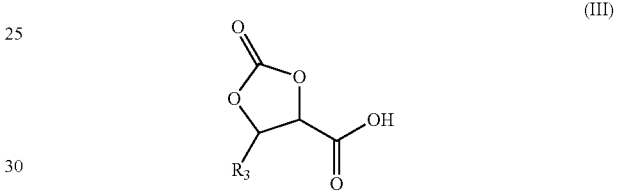

The present invention further provides a process for the preparation of a 2-exo-1,3-dioxolane-4-carboxamide of formula (I) which, according to one embodiment, is characterized in that a 2-oxo-1,3-dioxolane-4-carboxylic acid of formula (III) is reacted with an amine of the formula $R_1$—NH—$R_2$ to give the 2-oxo-1,3-dioxolane-4-carboxamide (I) according to the invention, where $R_1$, $R_2$ and $R_3$ have the meanings given. It is possible, by virtue of this reaction, to obtain 2-oxo-1,3-dioxolane-4-carboxamides of formula (I) wherein $R_1$ and $R_2$ are both different from H.

Since water is formed during this reaction, it is particularly advantageous to carry out the reaction in the presence of a water-withdrawing agent, in particular a carbodiimide.

According to another embodiment, the 2-oxo-1,3-dioxolane-4-carboxylic acid of formula (III) can also be reacted with an isocyanate of the formula $R_2$—NCO to give the 2-oxo-1,3-dioxolane-4-carboxamide (I) according to the invention, where $R_1$=H and $R_2$ and $R_3$ have the meanings given.

According to this embodiment, the 2-oxo-1,3-dioxolane-4-carboxylic acid of formula (III) can be reacted either with a monoisocyanate or with a polyisocyanate having n NCO groups, where n has the meaning given above.

The reaction is preferably carried out in the presence of catalyst selected from tertiary amines, organometallic compounds, and mixtures thereof. The tertiary amine can be selected e.g. from dimethylcyclohexylamine, 4-dimethylaminopyridine (DMAP), diaza cyclooctane (DABCO), and diazabicycloundecene (DBU); the organometallic compound can be selected e.g. from dibutyltin dilaurate (DBTL), a bismuth carboxylate such as bismuth octanoate or bismuth neodecanoate, a titanium or zirconium alkoxy-late or carboxylate, and the like catalysts known in the prior art.

In the case of the monoisocyanate of the formula $R_2$—NCO according to the invention, $R_2$ is preferably selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, phenyl and benzyl.

The polyisocyanate according to the invention is preferably an aliphatic isocyanate, an aromatic isocyanate or a combined aliphatic/aromatic isocyanate with a NCO functionality (number of NCO groups in the molecule) of n=2 to 5, preferably n=2 to 3.

Suitable polyisocyanates include tetramethylene 1,4-diisocyanate, 2-methylpenta-methylene 1,5-diisocyanate, hexamethylene 1,6-diisocyanate (HDI), 2,2,4- and 2,4,4-trimethylhexamethylene 1,6-diisocyanate (TMDI), dodecamethylene 1,12-diisocyanate, lysine diisocyanate and lysine ester diisocyanate, 1-isocyanato-3,3,5-trimethyl-5-isocyanatomethyl-cyclohexane (isophorone diisocyanate—IPDI), 1,4-diisocyanato-2,2,6-trimethylcyclohexane (TMCDI), 2,2'-, 2,4'- and 4,4'-dicyclohexylmethane diisocyanate ($H_{12}$MDI), cyclohexane 1,3-diisocyanate and cyclohexane 1,4-diisocyanate (CHDI), 1,3- and 1,4-bis(isocyanatomethyl)cyclohexane, 4,4'-diisocyanatodicyclohexyl-2,2-propane, m- and p-phenylene diisocyanate, 2,3,5,6-tetramethyl-1,4-diisocyanatobenzene, 3,3'-dimethyl-4,4'-diisocyanatodiphenyl (TODI), 2,4- and 2,6-tolylene diisocyanate (TDI), 2,2'-, 2,4'- and 4,4'-diphenylmethane diisocyanate (MDI), naphthalene 1,2-diisocyanate and naphthalene 1,5-diisocyanate (NDI), m- and p-xylylene diisocyanate (XDI), tetramethylxylylene diisocyanate (TMXDI), and also any desired mixtures of the aforementioned isocyanates.

For the purposes of the present invention, the polyisocyanates according to the invention are also intended to include dimers (uretdiones) and trimers (isocyanurates). Particular importance is attributed here to the HDI trimer. Furthermore, oligomers are also to be included, such as e.g. "polymeric MDI" where n=1 to 8:

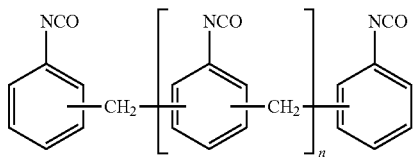

Moreover, prepolymers of polyisocyanates with polyols can also be used if a stoichiometric excess of NCO groups is present. Suitable polyols include polyoxyalkylene polyols (also called "polyether polyols"), which can contain inter alia ethylene oxide units, propylene oxide units and butylene oxide units, aliphatic diols and polyols, and also polyester polyols and polycarbonate polyols, castor oil, hydroxylated epoxidized soya oil, and also mixtures of the aforementioned polyols.

An exemplary, non-exhaustive overview of reaction products of 2-oxo-1,3-dioxolane-4-carboxylic acid with mono- and polyisocyanates is given in the formula scheme below:

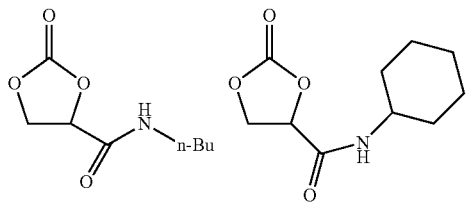

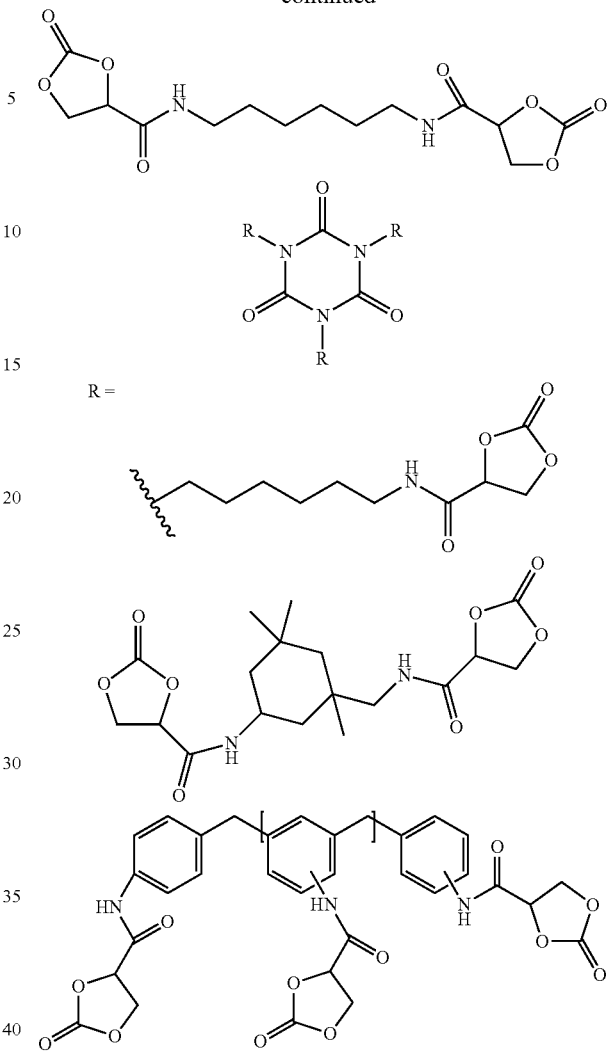

The present invention furthermore provides a process for the preparation of a 2-oxo-1,3-dioxolane-4-carboxylic acid of formula (III) hereinabove, which is a key intermediate in the preparation of the 2-oxo-1,3-dioxolane-4-carboxamide of the invention.

According to one embodiment, the 2-oxo-1,3-dioxolane-4-carboxylic acid of formula (III) can be prepared by hydrolysing a 2-oxo-1,3-dioxolane-4-carboxylic acid ester of formula (IV)

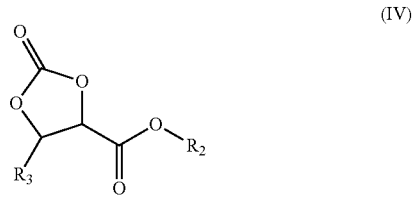

(IV)

where $R_2$ and $R_3$ have the meanings given, in an acidic medium, preferably in aqueous acetic acid.

It is also possible to arrive from the 2-oxo-1,3-dioxolane-4-carboxylic add ester of formula (IV) directly at the 2-oxo-1,3-dioxolane-4-carboxamide according to the invention of formula (I) by reacting the ester (IV) with a formamide of the formula $R_1R_2N$—CHO, where $R_1$ and $R_2$ have the meanings given.

Moreover, according to another embodiment, the 2-oxo-1,3-dioxolane-4-carboxylic acid of formula (III) can be prepared by oxidizing a glycerol carbonate of formula (V)

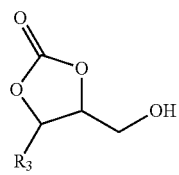

(V)

where $R_3$ has the meaning given, and more specifically for example by means of N-oxide-mediated oxidation, or by means of aerobic oxidation.

The N-oxide-mediated oxidation may be carried out with 1,3,5-trichloroisocyanuric acid and 2,2,6,6-tetramethylpiperidin-1-oxyl (TEMPO). It may also be carried out with hydrogen peroxide as an oxidant, e.g. in the presence of a manganese salt.

The aerobic oxidation uses oxygen from air or oxygen in pure form as the oxidant. It is suitably carried out in the presence of at least one transition metal salt selected from Co, Mn, Cu, Fe, and mixtures thereof, preferably Mn. It is preferably carried out in a suitable solvent or in (e.g. aqueous) acetic acid. The oxygen pressure should be in the range of 0.1 to 100 bar. The presence of an N-oxide such as TEMPO is preferred. The aerobic oxidation reaction is particularly preferred to oxidize glycerol carbonate (4-(hydroxymethyl)-2-oxo-1,3-dioxolane) to form 2-oxo-1,3-dioxolane-4-carboxylic acid. A source of oxygen may also be the decomposition reaction of hydrogen peroxide with e.g. manganese ions. Generally speaking, the aerobic oxidation reaction hereinabove elegantly solves the problem of providing a source of 2-oxo-1,3-dioxolane-4-carboxylic acid from glycerol carbonate.

The invention further provides the use of the 2-oxo-1,3-dioxolane-4-carboxamides according to the invention for the preparation of hydroxyurethanes. The amides according to the invention react, as has been shown in the formula scheme listed at the outset, with R'—$NH_2$ to give hydroxyurethanes. As in the case of the 2-oxo-1,3-dioxolane-4-carboxylic acid esters (PCT/EP2011/058945), hydroxyurethanes with secondary hydroxyl groups are predominantly formed here since during the attack of the nucleophilic nitrogen atom, the negative charge on the oxygen atom, which is closer to the $CONR_1R_2$ group, is better stabilized. Hydroxyurethanes with secondary hydroxyl groups have the advantage that no back-reaction takes place. Theoretically, an amine attack on the amide group would also be conceivable. However, it has been shown that the amine only attacks the 2-oxo-1,3-dioxolane group.

Suitable amines here are primary and secondary amines with alkyl groups, aryl groups, aralkyl groups and also alkaryl groups as radicals. Primary amines react more quickly than secondary amines; aliphatic amines react more quickly than aromatic amines. In particular, relatively high molecular weight (poly)amines such as e.g. Jeffamine® from Huntsman Corp. and polyetheramines from BASF SE are of suitability here.

In the case of primary amines with the formula R'—$NH_2$, the reaction can be shown as follows, with only the preferred reaction to give the hydroxyurethane with a secondary hydroxyl group being shown here:

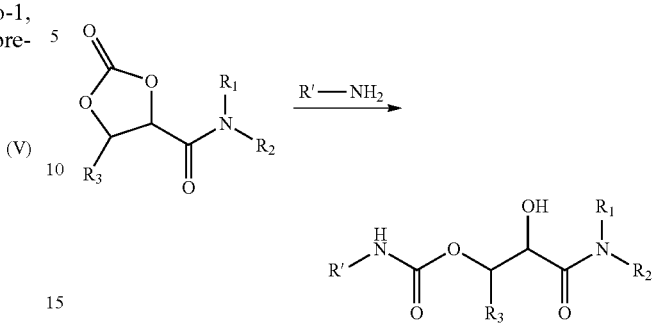

The invention further provides the use of the 2-oxo-1,3-dioxolane-4-carboxamides according to the invention for the preparation of hydroxycarbonates. The formula scheme below shows only the preferred reaction to give the hydroxycarbonate with a secondary hydroxyl group. Suitable alcohols of the formula R'—OH are in particular the aforementioned polyols.

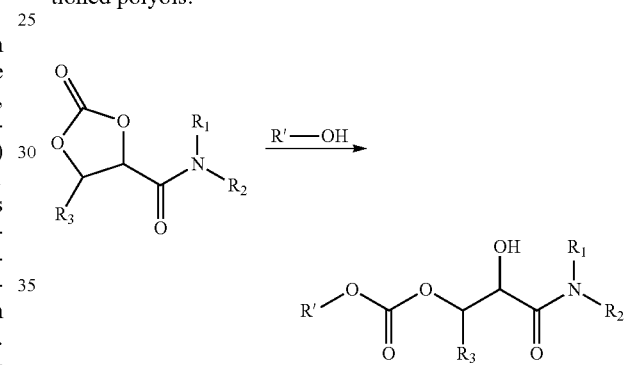

The invention further provides the use of the 2-oxo-1,3-dioxolane-4-carboxamides according to the invention for the preparation of hydroxysulphanylformates according an analogous formula scheme:

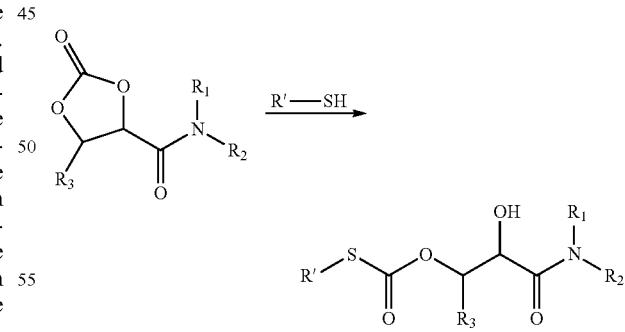

If both the amines, alcohols and/or thiols used and also the 2-oxo-1,3-dioxolane-4-carboxamides according to the invention are polyvalent (R2=n-valent radical with n–1 further 2-oxo-1,3-dioxolane-4-carboxamide groups), the reaction of the same leads to polymeric products, namely to polymeric hydroxyurethanes, hydroxycarbonates and/or hydroxysulphanylformates. In other words, polyvalent 2-oxo-1,3-dioxolane-4-carboxamide binders (where n>1) can be readily cured with polyamines, polyols and/or polythiols.

Accordingly, the present invention further consists in the use of the 2-oxo-1,3-dioxolane-4-carboxamides according to the invention for the preparation of polymeric hydroxyurethanes, hydroxycarbonates and/or hydroxysulphanylformates.

One advantage of polyhydroxyurethane systems lies in the relatively high hydrophilicity of these systems, which can be attributed to the OH groups present. These OH groups are in principle also available for the crosslinking with polyisocyanates, although the isocyanate-free systems possible according to the invention are preferred on account of their lower toxicity.

Moreover, when producing polyhydroxyurethane systems which are based on 2-oxo-1,3-dioxolanes, bubble formation as a result of $CO_2$ that is formed may not arise, even in the presence of moisture. Consequently, largely pore- and bubble-free coatings are possible, which is sometimes problematic for classic polyurethane systems. Furthermore, the thermal stability of such polyhydroxyurethane systems is also higher than the stability of classic polyurethane systems.

Moreover, the low molecular weight 2-oxo-1,3-dioxolane-4-carboxamides can be used to block amines as end groups (so-called "end caps"), which constitutes a further subject matter of the present invention. This is also of interest with regard to conventional, amine-crosslinked polyurethane systems since an amine excess can lead to discolorations, while an isocyanate excess is toxicologically unacceptable.

The present invention is now illustrated in more detail by reference to the examples hereinbelow.

Example 1

Preparation of
4-methoxycarbonyl-2-oxo-1,3-dioxolane (Reference)

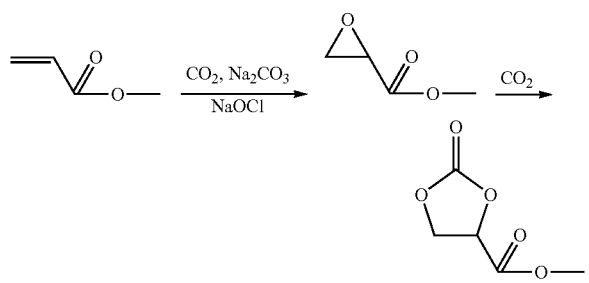

80 g of sodium carbonate were dissolved in 200 ml of distilled water in a 1000 ml three-neck flask. The solution was cooled to 10° C. 58.5 g of methyl acrylate were then added and, after ca. 10 minutes, likewise at 10° C., 400 ml of a 7% strength aqueous sodium hypochlorite solution were stirred in. Then, the system was immediately flushed intensively with $CO_2$. The temperature was allowed to increase to room temperature. The flask was flushed intensively with $CO_2$ for a further 1 h at ca. 25 to 30° C., during which the temperature was held in the stated range by means of occasional cooling with an ice bath. The resulting white solid was filtered off via a suction filter. The filtrate was extracted with 4×90 ml of dichloromethane. The combined organic phase was dried with sodium sulphate and filtered off. The filtrate was removed on a rotary evaporator. Methyl epoxypropionate was obtained in 50 to 60% yield and a purity of 97%.

20 g of the methyl epoxypropionate were mixed with 20 g of tert-butyl methyl ether and 1 g of tetrabutylammonium bromide. The homogeneous mixture was transferred to a 100 ml pressurized reactor and carboxylated for 4 days at 40° C. and a $CO_2$ pressure of 20 bar. After the carboxylation, a two-phase system was obtained; the upper phase consisted of tert-butyl methyl ether, and the lower phase consisted of 4-methoxycarbonyl-2-oxo-1,3-dioxolane (purity 94% (GC), yield 94%).

The product was characterized as follows: $^1$H NMR (500 MHz, CDCl$_3$): 3.82 (3H, s, CH$_3$), 4.50 (1H, dd, J=5.5, 9.0, CH$_2$), 4.66 (1H, dd, J=9.0, 9.0, CH$_2$), 5.09 (1H, dd, J=9.0, 5.5, CH); $^{13}$C NMR (125 MHz, CDCl$_3$): 53.81 (CH$_3$), 67.00 (CH$_2$), 72.34 (CH), 153.97 (—O—CO—O—), 167.42 (—CO—O—); IR (neat): 1812 cm$^{-1}$, (—O—00-O—), 1742 cm$^{-1}$ (—CO—O—).

Example 2

Preparation of
4-methoxycarbonyl-2-oxo-1,3-dioxolane (Reference)

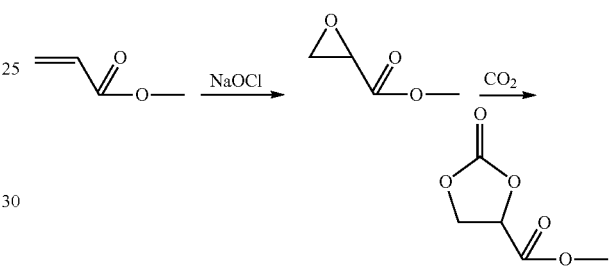

940 ml of a 7% strength aqueous sodium hypochlorite solution were introduced as initial charge in a 2000 ml three-neck flask. The solution was cooled to 0° C. with the help of an ice/salt water bath. 58.5 g of methyl acrylate were then added and the mixture was held at 0° C. for 30 minutes. The it w-temperature mixture was then removed and further stirred for ca. 1.5 h such that the mixture heated up by itself (65-70° C.). A colourless, cloudy solution was formed. Then, the solution was cooled to room temperature and extracted with 4×150 ml of dichloromethane. The combined organic phase was dried with magnesium sulphate and filtered off. The filtrate was removed on a rotary evaporator. Methyl epoxypropionate was obtained in 70 to 80% yield and a purity of 97%. The further reaction to give 4-methoxycarbonyl-2-oxo-1,3-dioxolane proceeded as described in Example 1.

Example 3

Preparation of
4-methoxycarbonyl-2-oxo-1,3-dioxolane (Reference)

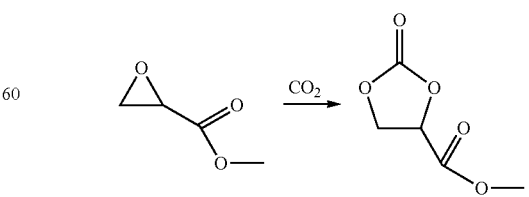

20 g of methyl epoxypropionate were mixed with 20 g of acetonitrile, 1.5 g of benzyltrimethylammonium chloride and 1.5 g of ZnBr₂. The homogeneous mixture was transferred to a 100 ml pressurized reactor and carboxylated for 6 days at 25° C. and a CO₂ pressure of 30 bar. After the carboxylation, the mixture was diluted with 100 g of acetonitrile. The mixture was purified with aluminium oxide and activated carbon. Then, the acetonitrile was distilled off. This gave 4-methoxycarbonyl-2-oxo-1,3-dioxolane (purity 72% (GC), yield 65%).

Example 4

Preparation of 4-methoxycarbonyl-2-oxo-1,3-dioxolane (Reference)

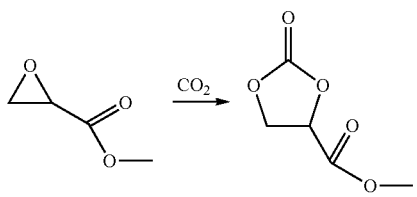

20 g of methyl epoxypropionate were mixed with 20 g of tert-butyl methyl ether, 1.5 g of tetrabutylammonium bromide and 1.5 g of potassium iodide. The homogeneous mixture was transferred to a 100 ml pressurized reactor and carboxylated for 6 days at 50° C. and a CO₂ pressure of 30 bar. After the carboxylation, a two-phase system was obtained; the upper phase consisted of tert-butyl methyl ether, and the lower phase consisted of 4-methoxycarbonyl-2-oxo-1,3-dioxolane (purity 83% (GC), yield 79%).

Example 5

Acidic hydrolysis of 4-methoxycarbonyl-2-oxo-1,3-dioxolane

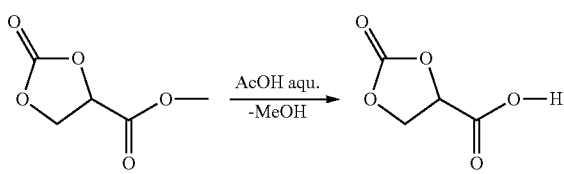

73 g (0.5 mol) of 4-methoxycarbonyl-2-oxo-1,3-dioxolane were heated under reflux for 3 hours with 11 g (0.55 mol) of water and 48 g (0.8 mol) of acetic acid. The mixture was then added to cyclohexane, the separated-off oil was carefully freed from all volatile constituents and the residue was ground with methylene chloride until a colourless crystalline precipitate had formed. The precipitate was washed with diethyl ether and dried in vacuo. This gave 2-oxo-1,3-dioxolane-4-carboxylic acid.

m.p.: 119-121° C. ¹H-NMR (CDCl₃DMSO-d6 (10.1 [mol/mol])): 9.486 (broad, s; 1H); 5.012 (dd; 1H); 4.637 (t; 1H); 4.506 (dd; 1H). ¹³C-NMR (CDCl₃/DMSO-d6 (10.1 [mol/mol])): 168.425 (CO acid); 153.348 (CO cyclocarbonate); 72.247 (CH—COOH); 66.988 (CH₂CH—COOH). IR (ν [cm⁻¹]): 2977 bs (OH acid), 2751 bw, 2658 bw, 2621 bw, 2538 bw, 2407 bw, 1785 bm (CO cyclocarbonate), 1793 bs (CO acid), 1546 w, 1481 w, 1431 w, 1399 s, 1345 w, 1325 w, 128 m, 1196 s, 1087 s, 1074 s, 1039 m, 928 w, 832 s, 769 s, 724 m, 699 s, 650 m, 633 s, 525 s.

Example 6

N-Oxide-Mediated Oxidation of Glycerol Carbonate

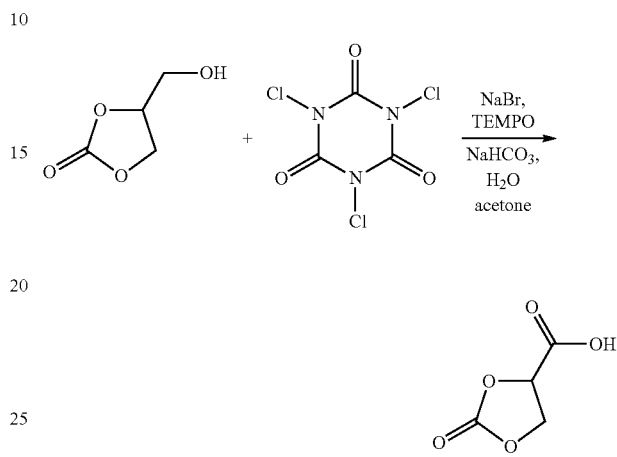

(Procedure analogous to JOC 2003; 68; pages 4999 ff.) 118.1 g (1 mol) of glycerol carbonate, 168 g (2 mol) of sodium hydrogencarbonate, 232 g (1 mol) of trichloroisocyanuric acid, 18 g (1 mol) of water, 1.5 g (0.01 mol) of TEMPO (2,2,6,6-tetramethylpiperidin-1-oxyl) and 5 g (0.05 mol) of NaBr were introduced as initial charge in 1.5 l of ace-tone at 0° C. with stirring. The mixture was left to warm to room temperature and stirred for a further 12 hours, after which it was filtered off. The filtrate was concentrated by evaporation. The resulting oil was heated at reflux with chloroform. This gave 2-oxo-1,3-dioxolane-4-carboxylic acid in 97% yield.

Example 7

Aerobic Oxidation of Glycerol Carbonate

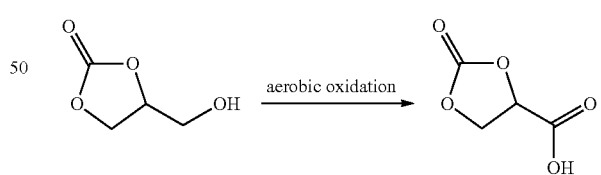

118 g (1 mol) of glycerol carbonate (4-(hydroxymethyl)-2-oxo-1,3-dioxolane), 16.3 g (0.1 mol) of N-hydroxyphthalimide, 7.8 g (0.045 mol) of m-chlorobenzoic acid and 1.3 g (0.05 mol) of cobalt(II) acetylacetonate were dissolved in 300 ml of glacial acetic acid and 1 l of ethyl acetate. The solution was saturated with oxygen and heated at reflux for 6 hours under an oxygen atmosphere. All volatile constituents were distilled off and the residue was ground with diethyl ether. Insoluble constituents were removed by means of washing with dichloromethane and toluene. This gave 2-oxo-1,3-dioxolane-4-carboxylic acid. The yield was about 15%.

Example 8

Aerobic Oxidation of Glycerol Carbonate

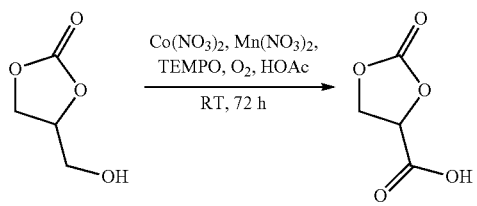 [SMILES: O=C1OCC(CO)O1 ; O=C1OCC(C(=O)O)O1]

11.81 g (0.1 mol) of glycerol carbonate (4-(hydroxymethyl)-2-oxo-1,3-dioxolane), 0.50 g (0.002 mol) of manganese(II) nitrate tetrahydrate ($Mn(NO_3)_2 \cdot 4H_2O$), 0.58 g (0.002 mol) of cobalt(II) nitrate hexahydrate ($Co(NO_3)_2 \cdot 6H_2O$) and 1.88 g (0.012 mol) of TEMPO (2,2,6,6-tetramethylpiperidin-1-oxyl) were dissolved in 100 ml of acetic acid. The reddish solution was stirred for 72 hours at room temperature under an oxygen atmosphere, evaporated to dryness, and the crude product was purified by recrystallization. This gave 2-oxo-1,3-dioxolane-4-carboxylic acid in the form of white to yellowish crystal needles. The yield was about 75%, and the analytical data were in agreement with the known data (Example 5).

Example 9

Reaction of 2-oxo-1,3-dioxolane-4-carboxylic acid with n-butyl isocyanate

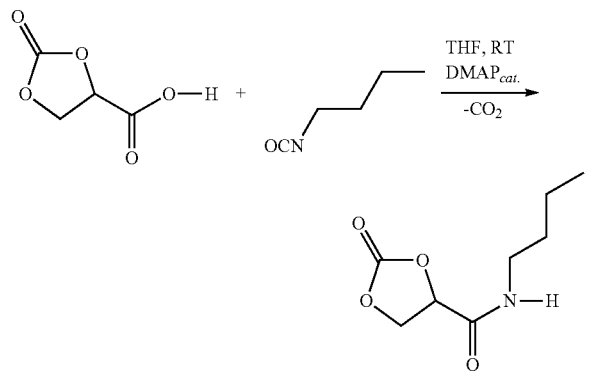

(The procedure was carried out analogously to Synthesis 2001; 2, pp. 243-246.) Equimolar amounts of 2-oxo-1,3-dioxolane-4-carboxylic acid (4.089 g; 37 mmol) and n-butyl isocyanate (3.67 g; 37 mmol) were dissolved in 100 ml of anhydrous THF. 1 mol % of DMAP (4-dimethylaminopyridine) was added and the mixture was stirred at room temperature until the IR spectrum indicated the disappearance of the isocyanate signal at 2050 cm$^{-1}$ and the appearance of an amine signal at 1690 cm$^{-1}$. After adding silicon dioxide, the mixture was filtered off and the solvent was removed. The residue was recrystallized from cyclohexane.

m.p.: 69-71° C. $^1$H-NMR (DMSO-d6): 8.454 (broad, s; 1H); 5.134 (dd; 1H); 4.676 (t; 1H); 4.412 (dd; 1H); 3.126 (dd; 2H); 1.438 (quint.; 2H); 1.302 (hex.; 2H); 0.895 (t; 3H). $^{13}$C-NMR (DMSO-d6): 165.836 (CO amide); 153.510 (CO cyclocarbonate); 73.103 (CH—CONHBu); 67.305 (CH$_2$CH—CONHBu); 38.267 (N—CH$_2$CH$_2$CH$_2$CH$_3$); 30.821 (N—CH$_2$CH$_2$CH$_2$CH$_3$); 19.534 (N—CH$_2$CH$_2$CH$_2$CH$_3$); 13.704 (N—CH$_2$CH$_2$CH$_2$CH$_3$). IR (v [cm$^{-1}$]): 3307 m (NH); 2959 m, 2933 m, 2873 m, 1780 s (CO cyclocarbonate), 1657 s (CO amide), 1561 s (CN amide) 1473 w, 1385 m, 1298 w, 1248 w, 1161 s, 1093 m, 1075 m, 1052 s, 999 w, 878 w, 820 w, 766 s, 740 w, 708 m, 672 s, 617 s.

Example 10

Reaction of 2-oxo-1,3-dioxolane-4-carboxylic acid with cyclohexyl isocyanate

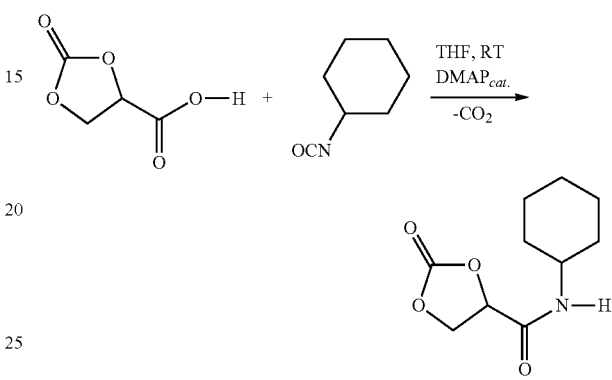

(The procedure was carried out analogously to Synthesis 2001; 2, pp. 243-246). 2.56 g (19 mmol) of 2-oxo-1,3-dioxolane-4-carboxylic acid and 2.42 g (19 mmol) of cyclohexyl isocyanate were dissolved in 50 ml of anhydrous THF. 0.05 g (1 mol %) of DMAP were added and the mixture was stirred overnight at room temperature, during which a colourless precipitate was formed. The solvent was removed and the residue was extracted with diethyl ether, from which the product crystallized out upon evaporation. This gave N-cyclohexyl-2-oxo-1,3-dioxolane-4-carboxamide.

m.p.: 123-125° C. $^1$H-NMR (CDCl$_3$/DMSO-d6 (10.1 [mol/mol])): 6.284 (broad, s: 1H); 5.007 (dd; 1H); 4.735 (t; 1H); 4.506 (dd; 1H); 3.803 (m; 1H); 1.935-1.232 (m; 10H). $^{13}$C-NMR (CDCl$_3$DMSO-d6 (10.1 [mol/mol])): 165.273 (CO amide); 153.002 (CO cyclocarbonate); 73.088 (CH—CONHCyHex); 67.077 (CH$_2$CH—CONHCyHex); 48.843 (NH—CH(CyHex)); 33.021 (CyHex); 32.952 (CyHex); 25.560 (CyHex); 25.110 (CyHex). IR (v [cm$^{-1}$]): 3284 bm (NH); 2933 m; 2909 m; 2852 m; 1807 s, 1790 s (CO cyclocarbonate); 1649 s (CO amide); 1544 s (CN); 1485 w; 1448 w; 1380 m; 1321 w; 1150 s; 1084 s; 1058 s; 1013 s; 934 w; 893 m; 869 w; 815 w; 767 s; 732 m; 689 m; 637 w; 529 m.

Example 11

Reaction of 2-oxo-1,3-dioxolane-4-carboxylic acid with HDI

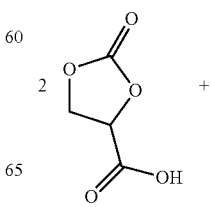

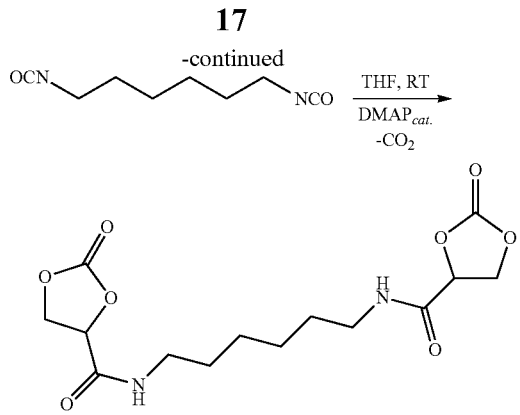

(The procedure was carried out analogously to Synthesis 2001; 2, pp. 243-246.) 9.55 g (57 mmol) of HDI and 0.14 g (14 mmol) of DMAP were dissolved in 20 ml of anhydrous THF. A solution of 15 g (140 mmol) of 2-oxo-1,3-dioxolane-4-carboxylic acid in 50 ml of anhydrous THF was added dropwise and the resulting mixture was stirred overnight at room temperature. The resulting precipitate was collected, washed with THF and ether and recrystallized from water. This gave the difunctional amide.

m.p.: 181-182° C. (decomposition). $^1$H-NMR (CDCl$_3$DMSO-d6 (10.1 [mol/mol])): 9.486 (broad, s; 1H); 5.012 (dd; 1H); 4.637 (t; 1H); 4.506 (dd; 1H). $^{13}$C-NMR (CDCl$_3$DMSO-d6 (10.1 [mol/mol])): 168.425 (CO acid); 153.348 (CO cyclocarbonate); 72.247 (CH—CONH-Bu-); 66.988 (CH$_2$CH—CONH-Bu-).

Example 12

Reaction of 2-oxo-1,3-dioxolane-4-carboxylic acid with trimeric HDI 80 g (0.16 mol) of HDI trimer (Desmodur® N3600, Bayer AG, or Basonat® LR 9046, BASF SE), 64 g (0.48 mol) of 2-oxo-1,3-dioxolane-4-carboxylic acid and 0.585 g (4.8 mmol) of DMAP were dissolved in one liter of THF and stirred overnight at room temperature. Then, 10 g of activated carbon and 5 mmol of acetic acid were added, and the mixture was stirred for a further hour. It was then filtered off and the solvent was distilled off.

This gave 130 g of a reddish oil, which was used for the subsequent curing experiments without further purification.

Viscosity: 35<500 mPas. IR (ν [cm$^{-1}$]): 3345, 2935, 2860, 1803, 1670, 1544, 1461, 1400, 1179, 1080, 747, 665. $^1$H-NMR (CDCl3); 7.21 (t; 1H); 4.952 (dd; 1H); 4.601 (t; 1H); 4.414 (dd; 1H); 3.698 (bs; 1H); 3.147 (decapl., 2H); 1.484 (wt, 2H); 1.416 (wt, 2H); 1.217 (bs, 4H). $^{13}$C-NMR (CDCl3); 166.109 (CONH); 153.089 (O—CO—O); 148.095 (N—CO—N), 77.194 (CH2-CH—CONH—), 73.057 (CH$_2$—CH—CONH—); 42.504; 39.156; 28.855; 27.474; 26.133 (the last 5 signals: -n-hex-).

Example 13

Curing Experiments with the Binder from Example 12

The binder resin from Example 12 was cured with customary amines, i.e. isophorone diamine (IPDA) and trimethyl hexamethylenediamine isomeric mixture (TMD). The results (given miscibility, potlife and Shore A hardness after 3 days of curing at room temperature) are shown in Table 1 below.

TABLE 1

| | Amine | Miscibility | Potlife | Shore A (3d) |
|---|---|---|---|---|
| IPDA | H₃C—cyclohexane with CH₃, CH₃, H₂N, NH₂ substituents | + | 5-10 min | 82 |
| TMD | H₂N—CH₂—C(CH₃)₂—CH₂—CH(CH₃)—CH₂—CH₂—NH₂ or H₂N—CH₂—CH(CH₃)—CH₂—C(CH₃)₂—CH₂—NH₂ | + | <5 min | 79 |

It is clear from the results given in Table 1 that the binder resin has a very high reactivity towards these amines, and the mechanical properties are also very good.

Example 14

In order to demonstrate the superiority of the carboxamides of the invention over the esters according to EP 2397474 A1, N-butyl-2-oxo-1,3-dioxolane-4-carboxamide and 2-oxo-1,3-dioxolane-4-carboxylic acid methyl ester were titrated with n-butylamine. In the case of the carboxamide 92±5 mole-% of amine was used up while in the case of the ester 114±5 mole-% of amine was used up. This demonstrates that noticeable aminolysis was going on with respect to the ester bond.

Moreover, Table 2 below gives the dynamic viscosities [mPas] of the reaction products obtained from the reaction products of two molecules of 2-oxo-1,3-dioxolane-4-carboxylic acid methyl ester with one molecule of 1,6-hexanediol ("hexanediol diester", "HDDE") and, respectively, of two molecules of 2-oxo-1,3-dioxolane-4-carboxylic add with one molecule of HDI ("hexamethylene diamide", "HMDA") with equimolar amounts of said customary amines, i.e. IPDA and TMD after seven days of curing at room temperature. The superiority of the carboxamide products is thus clearly demonstrated.

TABLE 2

|  | HDDE | HMDA |
|---|---|---|
| IPDA | 206.000 | 2.900.000 |
| TMD | 1.600.000 | 9.400.000 |

The invention claimed is:
1. 2-Oxo-1,3-dioxolane-4-carboxamide of formula (I),

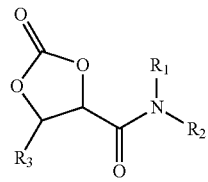

(I)

characterized in that
(i) $R_1$ and $R_2$, in each case independently of one another, are selected from H, straight-chain $C_{1-12}$ alkyl groups, branched or cyclic $C_{3-12}$ alkyl groups, $C_{6-10}$-aryl groups, $C_{6-12}$-ar-alkyl groups and $C_{6-12}$-alkaryl groups or, together with the N atom to which they are bonded, form a 5- to 8-membered ring, and $R_3$ is selected from H and straight-chain $C_{1-12}$ alkyl groups, branched or cyclic $C_{3-12}$ alkyl groups, or
(ii) $R_1$ and $R_3$ are each H, and $R_2$ is a radical having a valency of 2 to 5, which is substituted with an amount equal to the valency minus 1 of further 2-oxo-1,3-dioxolane-4-carboxamide groups of formula (II)

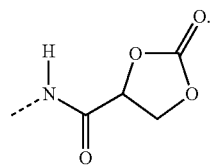

(II)

2. 2-Oxo-1,3-dioxolane-4-carboxamide according to claim 1, characterized in that $R_1$ and $R_3$ are each H, and $R_2$ is selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, phenyl and benzyl.

3. 2-Oxo-1,3-dioxolane-4-carboxamide according to claim 1, characterized in that the radical has a valency of 2 to 3.

4. 2-Oxo-1,3-dioxolane-4-carboxamide according to claim 1, characterized in that $R_2$ is selected from straight-chain or branched $C_{2-22}$-alkylene groups, polyether groups of the formula -$(A_1O)_m$—, wherein $A_1$ is $C_{2-5}$-alkylene and m is 1-100, polycarbonate groups, polyester groups, poly(meth)acrylate groups, and combinations thereof.

5. A process for the preparation of a 2-oxo-1,3-dioxolane-4-carboxamide as defined in claim 1, characterized in that a 2-oxo-1,3-dioxolane-4-carboxylic acid of formula (III)

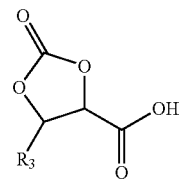

(III)

is reacted with an amine of the formula $R_1$—NH—$R_2$.

6. The process according to claim 5, characterized in that it is carried out in the presence of a water-withdrawing agent.

7. A process for the preparation of a 2-oxo-1,3-dioxolane-4-carboxamide as defined in claim 1, wherein $R_1$ is H, characterized in that a 2-oxo-1,3-dioxolane-4-carboxylic acid of formula (III) is reacted with an isocyanate of the formula $R_2$—NCO.

8. The process according to claim 7, characterized in that the isocyanate is a monoisocyanate or a polyisocyanate with 2 to 5 NCO groups.

9. The process according to claim 7, characterized in that the reaction is carried out in the presence of a catalyst selected from tertiary amines, organometallic compounds, and mixtures thereof.

10. A process for the preparation of a 2-oxo-1,3-dioxolane-4-carboxylic acid of formula (III)

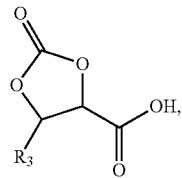

(III)

characterized in that a 2-oxo-1,3-dioxolane-4-carboxylic acid ester of formula (IV)

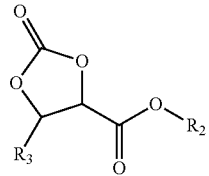

(IV)

is hydrolysed in an acidic medium,
where $R_2$ is selected from H, straight-chain $C_{1-12}$ alkyl groups, branched or cyclic $C_{3-12}$ alkyl groups, $C_{6-10}$-aryl groups, $C_{6-12}$-aralkyl groups and $C_{6-12}$-alkaryl groups, and $R_3$ is selected from H and straight-chain $C_{1-12}$ alkyl groups, branched or cyclic $C_{3-12}$ alkyl groups.

11. A process for the preparation of a 2-oxo-1,3-dioxolane-4-carboxylic acid of formula (III)

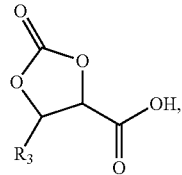

(III)

characterized in that a glycerol carbonate of formula (V)

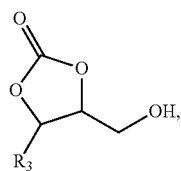

(V)

is oxidized, where $R_3$ is selected from H and straight-chain $C_{1-12}$ alkyl groups, branched or cyclic $C_{3-12}$ alkyl groups.

12. The process according to claim 11, characterized in that the oxidation is effected with a combination of 1,3,5-trichloroisocyanuric acid and an n-oxide, optionally 2,2,6,6-tetramethylpiperidin-1-oxyl.

13. The process according to claim 11, characterized in that the oxidation is effected as an aerobic oxidation.

14. A process of utilizing the 2-oxo-1,3-dioxolane-4-carboxamides as defined in claim 1 for the preparation of hydroxyurethanes, comprising reacting the 2-oxo-1,3-dioxolane-4-carboxamide with R'—NH$_2$, wherein R'—NH$_2$ is an amine.

15. A process of utilizing the 2-oxo-1,3-dioxolane-4-carboxamides as defined in claim 1 for the preparation of hydroxycarbonates, comprising reacting the 2-oxo-1,3-dioxolane-4-carboxamide with R'—OH, wherein R'—OH is an alcohol.

16. A process of utilizing the 2-oxo-1,3-dioxolane-4-carboxamides as defined in one of claim 1 for the preparation of hydroxysulfanylformates, comprising reacting the 2-oxo-1,3-dioxolane-4-carboxamide with R'—SH, wherein R'—SH is a thiol.

17. A process of utilizing the 2-oxo-1,3-dioxolane-4-carboxamides as defined in claim 1 for the preparation of polymeric hydroxyurethanes, hydroxycarbonates and/or hydroxysulfanylformates, comprising reacting polyvalent 2-oxo-1,3-dioxolane-4-carboxamide with R'—NH$_2$, R'—OH, or R'—SH, wherein R'—NH$_2$ is an amine, R'—OH is an alcohol, and R'—SH is a thiol.

18. A process of utilizing the 2-oxo-1,3-dioxolane-4-carboxamides as defined in claim 1 as end groups for the blocking of amines.

* * * * *